(12) United States Patent
Gliner et al.

(10) Patent No.: US 11,666,203 B2
(45) Date of Patent: Jun. 6, 2023

(54) USING A CAMERA WITH AN ENT TOOL

(71) Applicant: BIOSENSE WEBSTER (ISRAEL) LTD., Yokneam (IL)

(72) Inventors: Vadim Gliner, Haifa (IL); Assaf Govari, Haifa (IL); Yehuda Algawi, Binyamina (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 785 days.

(21) Appl. No.: 16/566,818

(22) Filed: Sep. 10, 2019

(65) Prior Publication Data

US 2020/0107701 A1 Apr. 9, 2020

Related U.S. Application Data (60) Provisional application No. 62/741,395, filed on Oct. 4, 2018.

(51) Int. Cl.
*A61B 1/00* (2006.01)
*A61B 90/00* (2016.01)
(Continued)

(52) U.S. Cl.
CPC ...... *A61B 1/00009* (2013.01); *A61B 1/00096* (2013.01); *A61B 1/00158* (2013.01);
(Continued)

(58) Field of Classification Search
CPC .............. A61B 1/00009; A61B 1/0005; A61B 1/00096; A61B 1/00158; A61B 1/00194; A61B 1/051; A61B 1/227; A61B 1/233; A61B 17/24; A61B 2034/2046; A61B 2034/2051; A61B 2034/2065; A61B 2034/2072; A61B 2090/309;
(Continued)

(56) References Cited

U.S. PATENT DOCUMENTS 7,211,042 B2 5/2007 Chatenever et al.
7,585,273 B2 9/2009 Adler et al.
(Continued)

FOREIGN PATENT DOCUMENTS

DE 29705973 6/1997

OTHER PUBLICATIONS

International Search Report dated Feb. 5, 2020 from corresponding PCT application PCT/IB2019/058068.

*Primary Examiner* — Michael T Rozanski
(74) *Attorney, Agent, or Firm* — Frost Brown Todd LLP (57) ABSTRACT

Apparatus, including a probe having an insertion tube and a section connected to the insertion tube. A camera is attached to the section and a magnetic field sensor coil, having a first coil axis of symmetry, is also attached with the first axis parallel to a camera direction of view. Another magnetic field sensor coil, which has a second coil axis of symmetry, is attached to the insertion tube with the second axis perpendicular to the camera direction of view. A processor receives signals generated by the coils and in response to signals received at a first time, identifies an initial orientation of an initial image produced by the camera. In response to signals received at a second, subsequent, time, the processor identifies a subsequent orientation of a subsequent image and rotates the subsequent image on a display so as to reorient the subsequent image to the initial orientation.

18 Claims, 9 Drawing Sheets

(51) Int. Cl.
 *A61B 5/06* (2006.01)
 *A61B 34/20* (2016.01)
 *A61B 1/227* (2006.01)
 *A61B 1/233* (2006.01)

(52) U.S. Cl.
 CPC .......... *A61B 1/00194* (2022.02); *A61B 5/062* (2013.01); *A61B 5/065* (2013.01); *A61B 34/20* (2016.02); *A61B 90/361* (2016.02); *A61B 1/227* (2013.01); *A61B 1/233* (2013.01); *A61B 2034/2046* (2016.02); *A61B 2090/364* (2016.02); *A61B 2090/3762* (2016.02)

(58) Field of Classification Search
 CPC ........ A61B 2090/364; A61B 2090/365; A61B 2090/3762; A61B 34/20; A61B 5/062; A61B 5/065; A61B 5/7425; A61B 90/361
 See application file for complete search history.

(56) References Cited

U.S. PATENT DOCUMENTS

| | | |
|---|---|---|
| 7,901,348 B2 | 3/2011 | Soper et al. |
| 9,782,159 B2 | 10/2017 | Tesar |
| 2008/0108870 A1 | 5/2008 | Wiita et al. |

USING A CAMERA WITH AN ENT TOOL

CROSS-REFERENCE TO RELATED APPLICATIONS

This application claims the benefit of U.S. Provisional Patent Application 62/741,395, filed Oct. 4, 2018, which is incorporated herein by reference.

FIELD OF THE INVENTION

This invention relates generally to surgical tools, and specifically to ENT (Ear, Nose, and Throat) tools incorporating a camera.

BACKGROUND OF THE INVENTION

The sinuses of a human patient are typically narrow tortuous passages that are difficult to navigate. This means that it is not easy to steer an ENT tool for optical inspection of the sinuses. The navigation is typically further complicated if, when a camera used for the inspection is rotated, motion of the tool as it is held by a physician performing the inspection causes images from the camera to be mis-oriented. The images are presented to a physician on a screen, and rotation of the camera may cause left-right motion of the camera and/or tool to display on the screen as up-down or right-left motion.

U.S. Pat. No. 7,585,273 to Adler et al., describes an invasive probe having opposite distal and proximal ends. The probe includes a transmitter, which is arranged to transmit an energy field, and a receiver, which is arranged to receive the energy field, and the transmitter and the receiver are disposed at the opposite ends of the probe. A control unit is adapted to determine an orientation of the distal end relative to the proximal end responsively to the energy field received by the receiver.

SUMMARY OF THE INVENTION

An embodiment of the present invention provides apparatus, including:

a probe, configured to be inserted into an aperture of a human patient, the probe consisting of:

an insertion tube;

a tubular deflectable section connected distally to the insertion tube;

a camera, attached to the tubular deflectable section and having a direction of view;

a first magnetic field sensor coil, which has a first coil axis of symmetry and is attached to the tubular deflectable section with the first axis parallel to the direction of view of the camera; and a second magnetic field sensor coil, which has a second coil axis of symmetry and is attached to the insertion tube with the second axis perpendicular to the direction of view of the camera;

a display, coupled to display images output by the camera; and a processor, which is coupled to receive signals generated by the first and second sensor coils in response to a magnetic field traversing the coils, and is configured:

in response to the signals received at a first time, to identify an initial orientation of an initial image produced by the camera, in response to the signals received at a second time, subsequent to the first time, to identify a subsequent orientation of a subsequent image produced by the camera, and to rotate the subsequent image on the display so as to reorient the subsequent image to the initial orientation.

In a disclosed embodiment the apparatus includes a third magnetic field sensor coil which has a third coil axis of symmetry and which is attached to the insertion tube with the third axis perpendicular to the direction of view of the camera and to the second coil axis of symmetry, and wherein the signals received by the processor also consist of signals generated by the third sensor coil in response to the magnetic field traversing the third coil.

In a further disclosed embodiment the apparatus includes a flexible printed circuit board (PCB) fixedly positioned within the deflectable tubular section and wherein the camera is fixedly attached to a distal termination of the flexible PCB. The flexible PCB may extend into the insertion tube.

In a yet further disclosed embodiment the processor is configured to determine a signal-based camera rotation in response to the signals received at the first and second times, and the processor is further configured to compare and analyze the initial and the subsequent images so as to determine an image-based camera rotation, and rotating the subsequent image includes applying an average of the signal-based camera rotation and the image-based camera rotation to reorient the subsequent image. Analyzing the initial and subsequent images may include filtering the images to remove translation of the camera.

In an alternative embodiment the apparatus includes a magnetic tracking system generating the magnetic field, and the processor is configured:

to register a computerized tomography (CT) image of the patient with the magnetic tracking system;

to determine a direction of view and a position of the camera in response to the signals received at the second time;

to receive an optical image acquired by the camera while the camera is directed towards the direction of view;

to analyze the CT image, using the direction of view and the position of the camera, to find an opaque surface in the CT image that is in a field of view of the camera; and to overlay the optical image on the opaque surface to texture map the opaque surface in the CT image.

There is further provided, in another embodiment of the present invention, a method for applying texture mapping to a computerized tomography (CT) image of a human patient, including:

registering the CT image with a magnetic tracking system configured to track a magnetic field sensor in the patient;

inserting a camera coupled to the magnetic field sensor into an aperture of the patient;

determining a direction of view and a position of the camera in response to signals received from the magnetic field sensor;

receiving an optical image acquired by the camera while the camera is directed towards the direction of view;

analyzing the CT image, using the direction of view and the position of the camera, to find an opaque surface in the CT image that is in a field of view of the camera; and overlaying the optical image on the opaque surface to texture map the opaque surface in the CT image.

Receiving the optical image may consist of positioning the camera and the field of view of the camera in a transparent region.

There is yet further provided in another embodiment of the present invention a method, including:

connecting a tubular deflectable section of a probe distally to an insertion tube of the probe;

attaching a camera to the tubular deflectable section, the camera having a direction of view;

attaching a first magnetic field sensor coil, which has a first coil axis of symmetry, to the tubular deflectable section with the first axis parallel to the direction of view of the camera;

attaching a second magnetic field sensor coil, which has a second coil axis of symmetry, to the insertion tube with the second axis perpendicular to the direction of view of the camera;

inserting the probe into an aperture of a human patient;

providing a display, coupled to display images output by the camera;

receiving signals generated by the first and second sensor coils in response to a magnetic field traversing the coils;

in response to the signals received at a first time, identifying an initial orientation of an initial image produced by the camera;

in response to the signals received at a second time, subsequent to the first time, identifying a subsequent orientation of a subsequent image produced by the camera; and rotating the subsequent image on the display so as to reorient the subsequent image to the initial orientation.

There is yet further provided, in another embodiment of the present invention, apparatus, including:

a magnetic tracking system generating a magnetic field within a human patient;

a probe, configured to be inserted into an aperture of the human patient;

a camera, attached to the probe and having a direction of view;

a magnetic field sensor coupled to the camera and configured to generate signals in response the magnetic field traversing the sensor;

a display, coupled to display images; and a processor, which is coupled to receive the signals, and is configured:

to register a computerized tomography (CT) image of the patient with the magnetic tracking system;

to determine a direction of view and a position of the camera in response to the signals;

to receive an optical image acquired by the camera while the camera is directed towards the direction of view;

to analyze the CT image, using the direction of view and the position of the camera, to find an opaque surface in the CT image that is in a field of view of the camera;

to overlay the optical image on the opaque surface to texture map the opaque surface in the CT image; and to present the texture mapped CT image on the display.

The present disclosure will be more fully understood from the following detailed description of the embodiments thereof, taken together with the drawings, in which:

DETAILED DESCRIPTION OF EMBODIMENTS

Overview

One of the problems encountered when inserting a camera into an aperture of a patient occurs when the camera is rotated. For example, the camera may be incorporated in an ENT tool that is inserted into a patient's nostril in order to view the sinuses of the patient, and to provide a good view, the camera may need to be rotated. The image produced by the camera is presented on a screen, but if the camera is rotated then subsequent motions of the tool, such as a left-to-right motion, may be misoriented, and may appear on the screen as being up and down or right-to-left.

Embodiments of the present invention correct the image presented on the screen for any rotation of the camera.

In one embodiment a probe that is used as an ENT tool has a deflectable tubular section at a distal part of the probe. An insertion tube, at a proximal part of the probe, is connected to the tubular section. A camera, defining a direction of view, is fixedly attached to a distal region of the tubular section, and a first magnetic field sensor coil is also fixedly attached to the distal region of the tubular section, so that an axis of symmetry of the coil is parallel to the direction of view of the camera. A second magnetic field sensor coil is fixedly attached to the rotatable tube so that the coil's axis of symmetry is perpendicular to the direction of view of the camera.

A display is coupled to display images output by the camera.

A processor is coupled to receive signals generated by the first and second sensor coils in response to a magnetic field traversing the coils. The processor is also configured to use the signals to identify an initial orientation of an initial image produced by the camera at a first time, and to use the signals to identify a subsequent orientation of a subsequent image produced by the camera at a second time. The processor may then rotate the subsequent image on the display so as to reorient the subsequent image to the initial orientation.

Thus, when the probe is placed in a magnetic field tracking system generating the magnetic field referred to above, the processor is able to use the signals from the sensors to determine quantitatively any rotation of the camera, and apply a corresponding rotation to the image presented on the display, so as to prevent misorientation of the presented image.

In a second embodiment, the images acquired by the camera are analyzed. A first image may be presented on a screen and may be selected as an "orientation-defining" image. Subsequent images are then acquired and analyzed to determine if any camera rotation has occurred. If a rotation has occurred it is quantified, and a corresponding rotation is applied to the acquired image so that a rotated acquired image is presented on the screen that maintains the defined orientation.

In a third embodiment, texture mapping is applied to a computerized tomography (CT) image of a patient. The CT image is registered with a magnetic tracking system that is configured to track a magnetic sensor in the patient. A camera coupled to the magnetic sensor is then inserted into an aperture of the patient, and signals from the sensor give a direction of view and a position of the camera. The camera provides an optical image while it is directed towards its direction of view.

A processor applies the direction of view and position of the camera to analyze the CT image, so as to find an opaque surface in the CT image that is in a field of view of the camera. The processor then overlays the optical image on the opaque surface to as to texture map the opaque surface.

System Description

In the following description, like elements in the drawings are identified by like numerals, and like elements are differentiated as necessary by appending a letter to the identifying numeral.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%.

Figure 1:
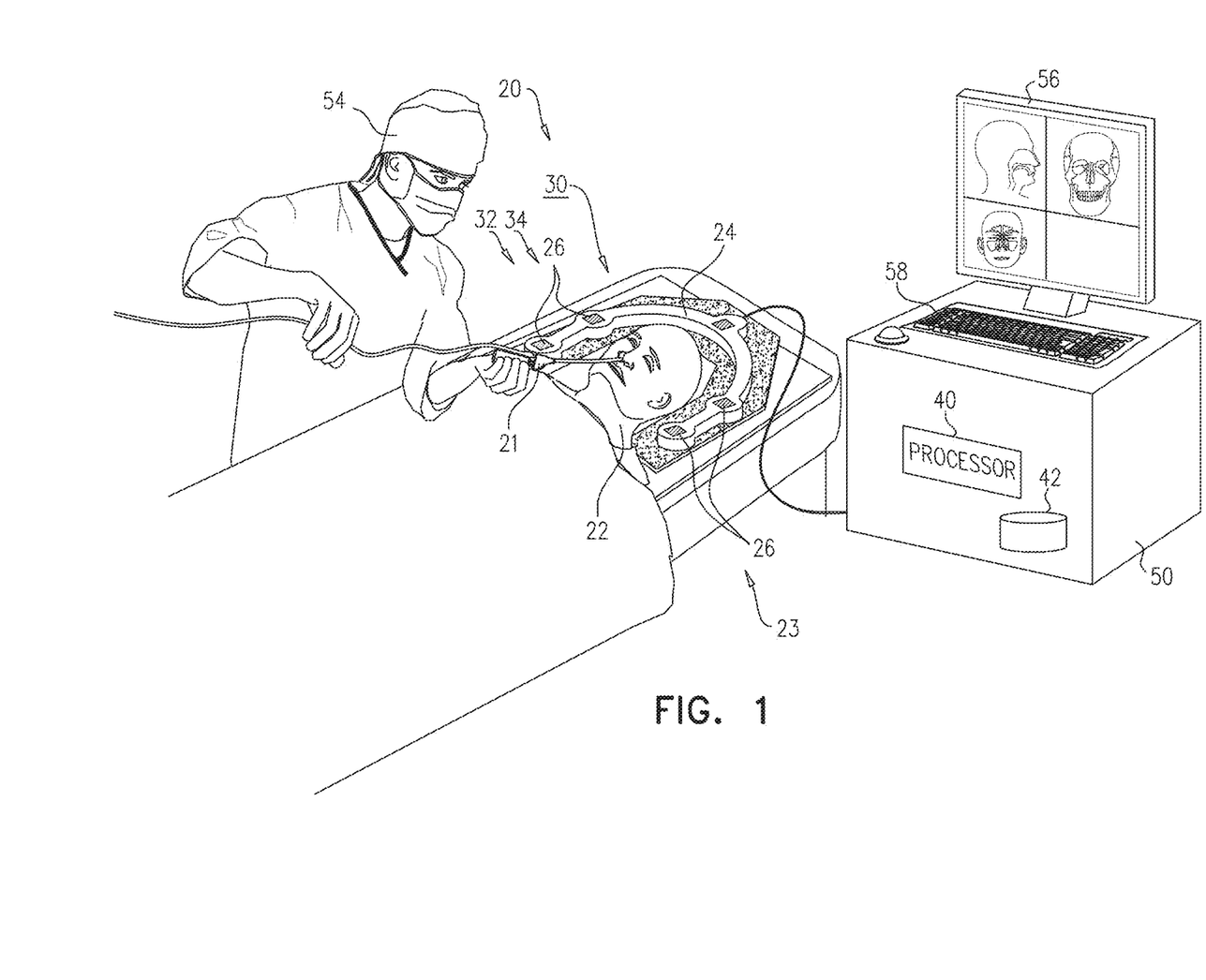
FIG. 1 is a schematic illustration of an ENT (ear, nose, and throat) system, according to an embodiment of the present invention.

Reference is now made to FIG. 1, which is a schematic illustration of an ENT (ear, nose, and throat) system 20, according to an embodiment of the present invention. In the following description an ENT tool 21 in system 20 is assumed to be used to perform a balloon sinuplasty procedure on a patient 22, although it will be understood that the tool may be used to perform other procedures on the patient.

As is described below, in one embodiment tool 21 comprises a single axis coil 32 and a dual axis coil 34 which act as magnetic field sensors and which are tracked during the procedure by a magnetic tracking system 23. For the tracking to be effective, in system 20 frames of reference of a CT (computerized tomography) image of patient 22 and of magnetic tracking system 23 are registered. While the CT image may typically comprise a magnetic resonance imaging (MRI) image or a fluoroscopic image, in the description herein the image is assumed to comprise, by way of example, a fluoroscopic CT image.

Prior to and during the sinus procedure, a magnetic radiator assembly 24, comprised in the magnetic tracking system, is positioned in proximity to the patient's head. Assembly 24 comprises magnetic field radiators 26 which are fixed in position and which transmit alternating magnetic fields into a region 30 wherein the head of patient 22 is located. Potentials generated by single axis coil 32 in region 30, in response to the magnetic fields, enable its position and its orientation to be measured in the magnetic tracking system's frame of reference. The position can be measured in three linear dimensions (3D), and the orientation can be measured for two axes that are orthogonal to the axis of symmetry of the single axis coil. However, the orientation of coil 32 with respect to its axis of symmetry cannot be determined from the potentials generated by the coil.

The same is true for each of the two coils of dual axis coil 34. I.e., for each coil the position in 3D can be measured, as can the orientation with respect to two axes that are orthogonal to the coil axis of symmetry, but the orientation of the coil with respect to its axis of symmetry cannot be determined.

By way of example, radiators 26 of assembly 24 are arranged in an approximately horseshoe shape around the head of patient 22. However, alternate configurations for the radiators of assembly 24 will be apparent, and all such configurations are assumed to be comprised within the scope of the present invention.

Prior to the procedure, the registration of the frames of reference of the magnetic tracking system with the CT image may be performed by positioning a magnetic sensor at known positions, such as the tip of the patient's nose, of the image. However, any other convenient system for registration of the frames of reference may be used.

Elements of system 20, including radiators 26 and coils 32 and 34, are under overall control of a system processor 40. Processor 40 may be mounted in a console 50, which comprises operating controls 58 that typically include a keypad and/or a pointing device such as a mouse or trackball. Console 50 connects to the radiators and to coils 32 and 34 via one or more cables and/or wirelessly. A physician 54 uses operating controls 58 to interact with the processor while performing the ENT procedure using system 20. While performing the procedure, the processor may present results of the procedure on a display 56, also herein termed screen 56.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Figure 2:
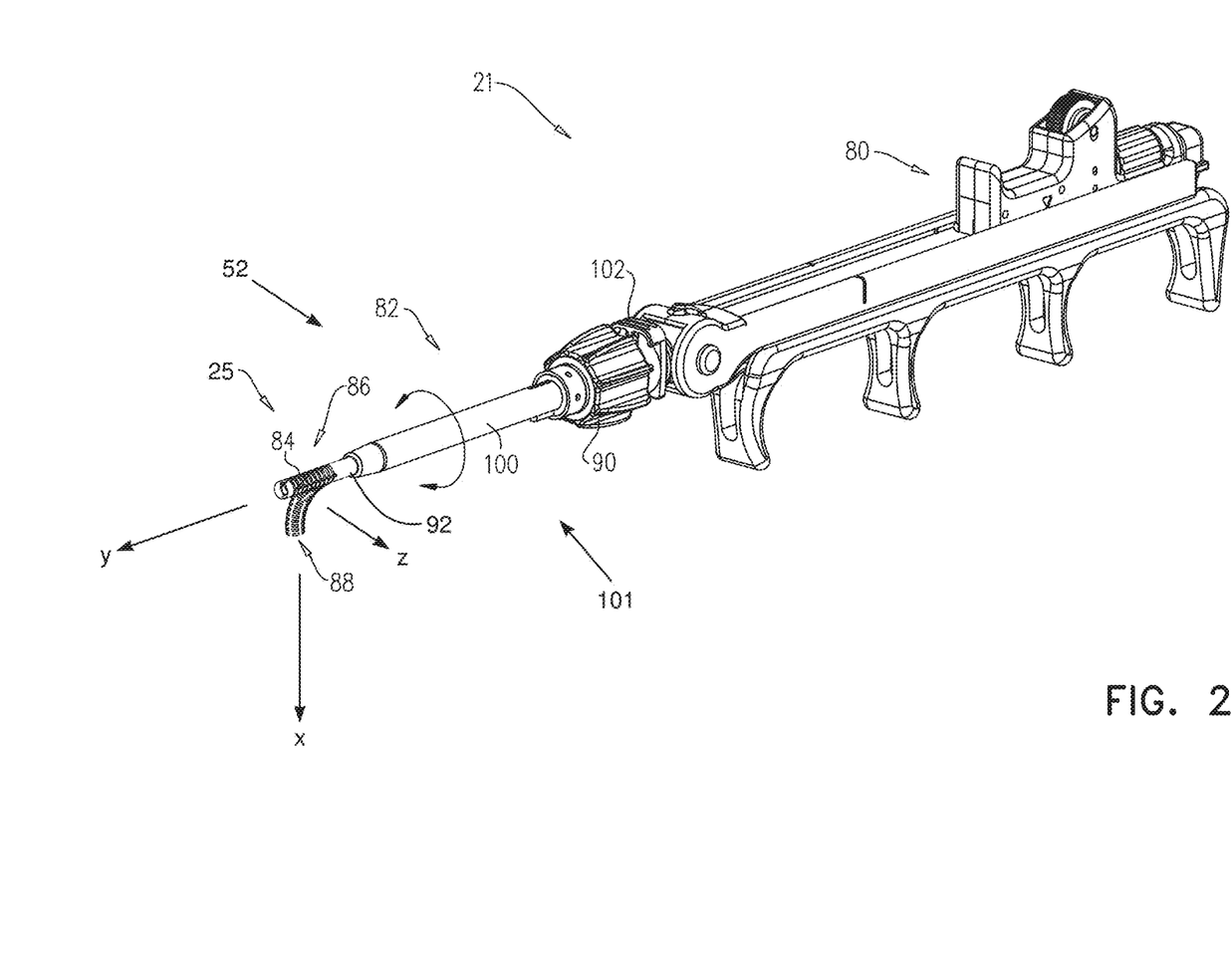
FIG. 2 is a schematic diagram of a tool used in the system, according to an embodiment of the present invention.
Figure 3:
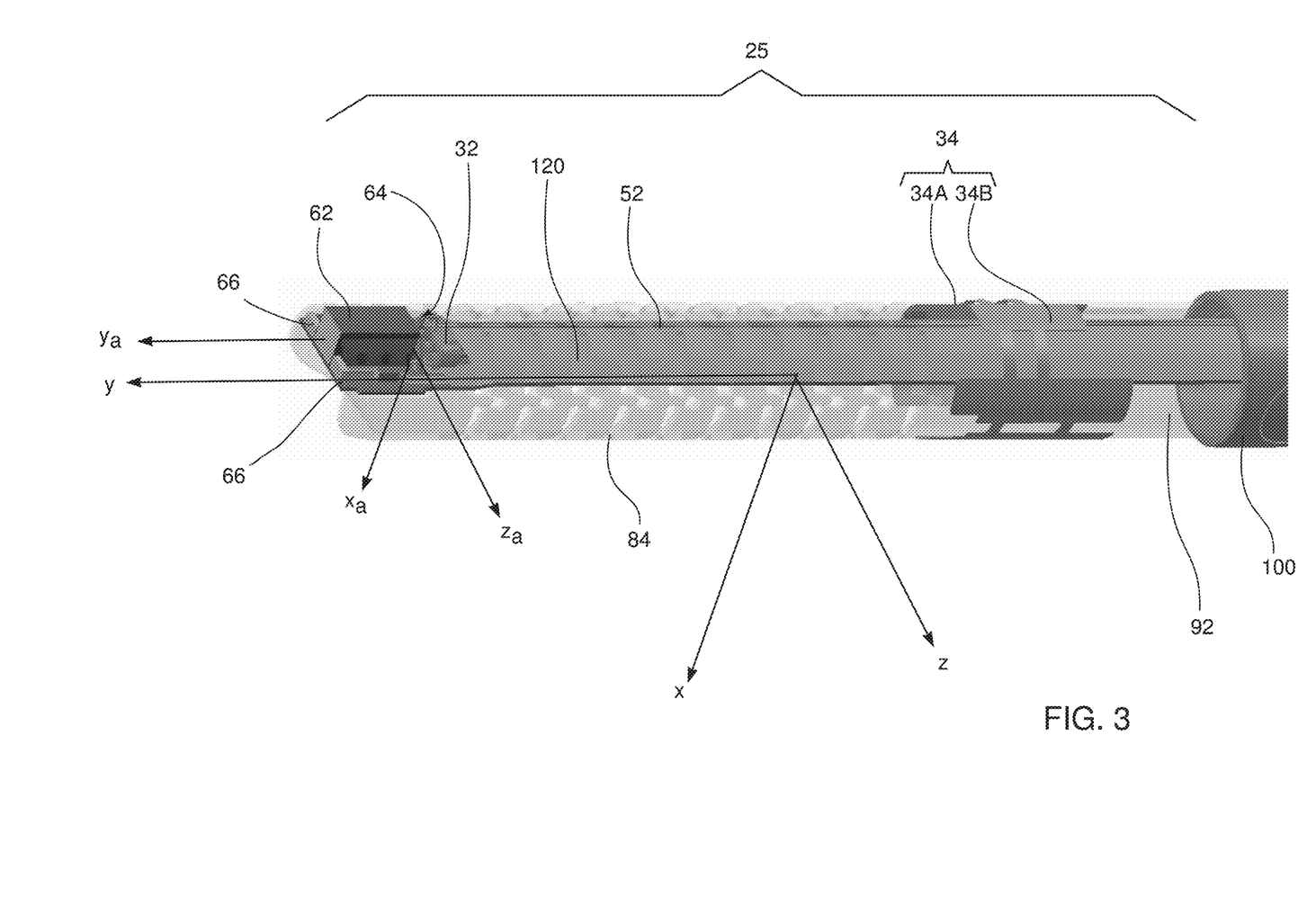
FIG. 3 is a schematic diagram of a distal end of the tool, according to an embodiment of the present invention.

FIG. 2 is a schematic diagram of tool 21 and FIG. 3 is a schematic diagram of a distal end 25 of the tool, according to an embodiment of the present invention. Tool 21 comprises a proximal section 80 and a distal section 82 which are connected together, but the distal section may be disassembled and removed from the proximal section.

Distal end 25 is also referred to herein as probe 25. In probe 25 distal section 82 comprises an articulated tubular section 84, which may be adjustably bent from a straight configuration 86 to a curved configuration 88, the latter being schematically shown in FIG. 2 by broken lines. In its straight configuration tubular section 84 has an axis of symmetry y. The curved configuration occurs in a plane comprising axis y and an x axis, orthogonal to the y-axis. In the description herein there is assumed to be a z axis, orthogonal to both the y and x axes.

The adjustment from the straight to the bent configuration, and vice versa, may be performed by applying tension to, and releasing tension on, a wire 52 by rotating a knob 90. As is also explained below, wire 52 extends from distal end 25 to knob 90.

Tubular section 84 is fixedly connected at its non-articulated proximal end 92 to an insertion tube 100 which may be rotated about axis of symmetry y, as indicated by the double headed arrow in FIG. 2. The rotation of tube 100 may be implemented by rotating knob 90. Knob 90 thus performs two functions: bending of articulated section 84, and rotation of tube 100. Which function is performed is according to the position of a sliding control 102. In a first position of the control rotation of knob 90 causes articulated section 84 to deflect, while tube 100 is stationary. In a second position of the control rotation of the knob causes tube 100 to rotate, with the knob about the tube axis of symmetry, while section 84 remains in its deflected (or undeflected) state.

Tube 100 and section 84 together form a tubular probe 101, and the probe is dimensioned to be insertable into an orifice of patient 22, such as a nostril and/or a sinus of the patient.

A generally rectangular flexible printed circuit board (PCB) 120 is fixedly positioned within tubular section 84, and extends proximally into proximal section 80. PCB 120 is aligned in an xy plane, so that when the tubular section bends into its curved configuration, the PCB bends with it. The PCB divides section 84 into an upper region and a lower region, and the lower region is able to act as a working channel which permits the passage of elements such as a guidewire, a balloon sinuplasty mechanism, and one or more fluids from proximal section 80, through the channel. The functioning of these elements is not relevant to embodiments of the present invention, and so for brevity the functioning is not described herein.

A camera 62 is mounted on an upper surface of distal termination of PCB 120, and the camera is assumed to have a planar rectangular array 64 of optical sensors, the array having edges parallel to the x and z axes of section 84, and thus being orthogonal to the y-axis. Array 64 is assumed to have a set of $x_a y_a z_a$ axes which are parallel to the xyz axes of section 84, and which have their origin at the center of array 64. In one embodiment camera 62 has a field of view (FOV) of approximately ±30° for an overall FOV of approximately 60°.

Light emitting diodes (LEDs) 66 are mounted on the PCB upper surface, and the LEDs provide illumination for images to be formed on array 64 when section 84 is inserted into patient 22.

Single axis sensor coil 32 is also mounted at the distal termination of PCB 120, on its upper surface, and the coil is mounted so that its axis of symmetry is parallel to axis of symmetry y of section 84.

Dual axis coil 34 is formed on a surface of non-articulated proximal end 92, typically by plating onto the surface. In the embodiment described herein dual axis coil 34 comprises two sensor coils 34A, 34B that are approximately planar, and that are configured so that their axes of symmetry are orthogonal to each other, and also orthogonal, i.e., perpendicular, to the axis of symmetry of single axis coil 32. In the description herein sensor coils 34A, 34B are assumed to have their axes of symmetry respectively parallel to the x and z axes of section 84.

In some embodiments only one sensor, herein assumed to be coil 34A, is present. The following description assumes that coils 34A, 34B are present as dual axis coil 34, and the description may be adapted, mutatis mutandis, for the case when only a single coil 34A is present.

Connecting conductors for the sensor coils, the camera, and the LEDs are formed on PCB 120, and the conductors transfer signals between these elements and proximal section 80 and processor 40.

Figures 4A, 4B:
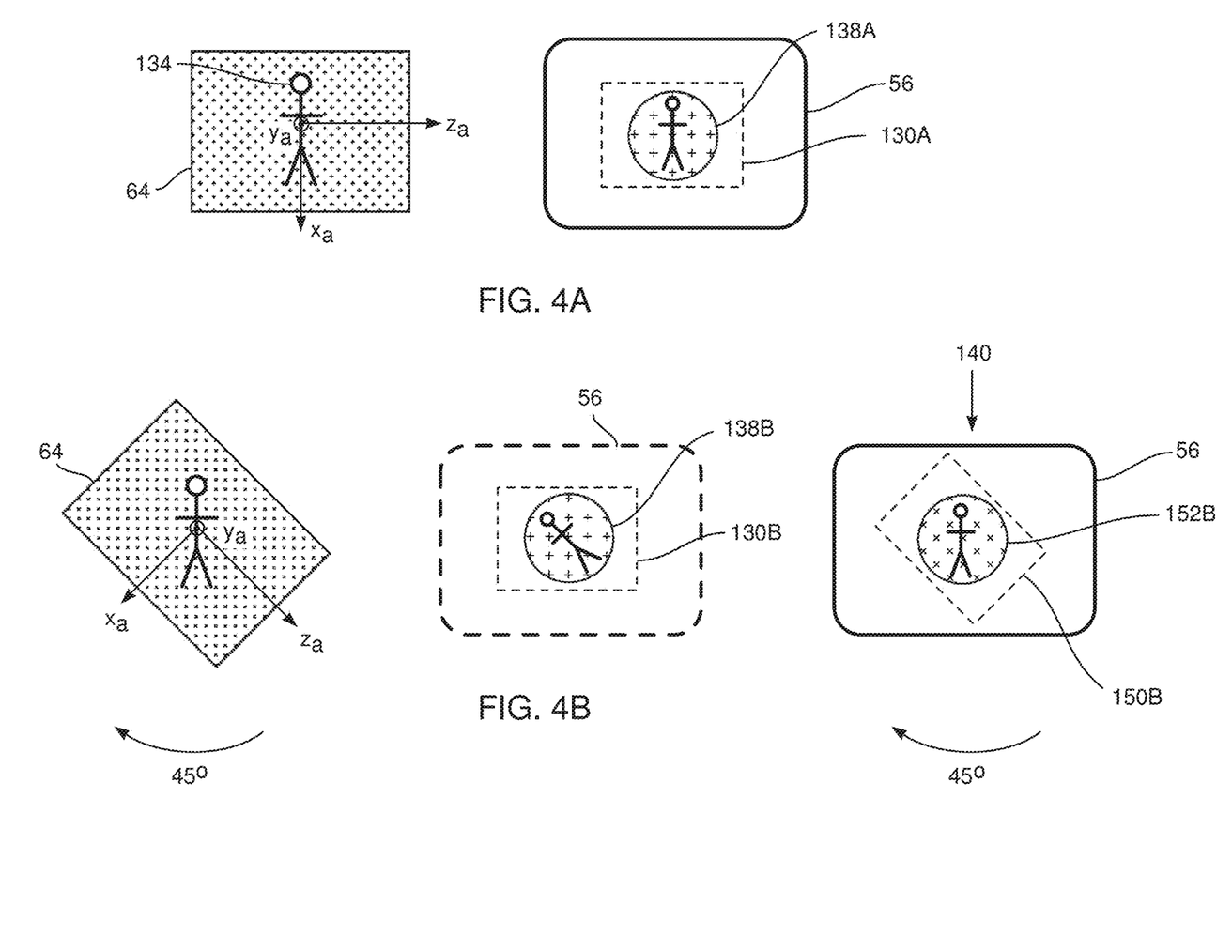
FIGS. 4A, 4B, 4C illustrate images formed on an array, and how the images are displayed on a screen, according to an embodiment of the present invention.
Figure 4C:
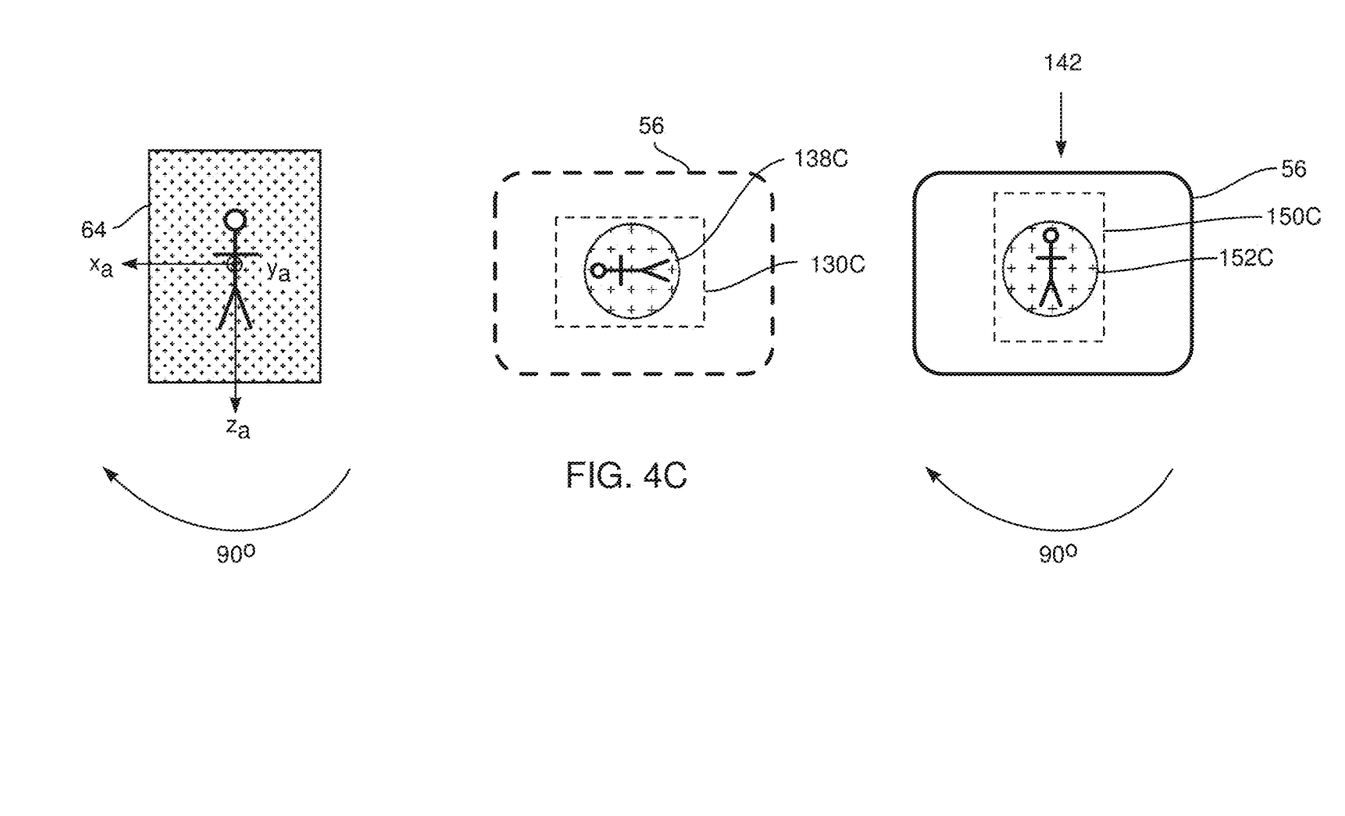

FIGS. 4A, 4B, 4C illustrate images formed on array 64, and how the images are displayed on screen 56, according to an embodiment of the present invention. In all diagrams array 64 is assumed to be rectangular with a larger dimension parallel to the $z_a$ axis of the array. The images produced by the array are displayed on screen 56, which is assumed have its horizontal dimension greater than its vertical dimension. I.e., screen 56 is assumed to be in a landscape orientation.

While screen 56 cannot rotate, array 64 is able to rotate, for example it is able to rotate around axis $y_a$.

FIG. 4A illustrates the situation where array 64 has not rotated around axis $y_a$. In this case an image 130A of the array is displayed on screen 56 with elements of a scene viewed by the array, such as a stick FIG. 134, unchanged with respect to rotation of the scene. In some embodiments the whole image produced by array 64 is not displayed on screen 56, but rather a central section of the image, as exemplified by a circular section 138A.

FIG. 4B illustrates the situation where array 64 has rotated 45° clockwise around the $y_a$ axis. In this case an image 130B of the array is displayed on screen 56 with elements of the scene viewed by the array, such as stick FIG. 134, rotated by 45° in a counter-clockwise direction. A circular region 138B may be displayed, and this illustrates the 45° rotation.

FIG. 4C illustrates the situation where array 64 has rotated 90° clockwise around the $y_a$ axis. In this case an image 130C of the array is displayed on screen 56 with elements of the scene viewed by the array, such as stick FIG. 134, rotated by 90° in a counter-clockwise direction. A circular region 138C illustrates the 90° rotation.

Screen 56 in the sections of FIGS. 4B and 4C referred to above has been drawn with broken lines to indicate that this is not the final display, as seen by physician 54 when looking at screen 56, and that images 130B and 130C are virtual images. Rather, in embodiments of the present invention the display seen by the physician is illustrated in a section 140 of FIG. 4B and a section 142 of FIG. 4C, where screen 46 has been drawn with solid lines.

As illustrated in FIG. 4B, embodiments of the present invention rotate virtual image 130B 45° clockwise to form a displayed image 150B with a circular region 152B. Similarly, as illustrated in FIG. 4C, embodiments of the present invention rotate virtual image 130C 90° clockwise to form a displayed image 150C with a circular region 152C.

While sections 140 and 142 illustrate that rotations of array 64 by 45° and 90° are cancelled out by corresponding rotations of the displayed image, it will be appreciated that in general a rotation of array 64 by any angle θ can be cancelled out by a rotation θ of the displayed image.

Thus, during a procedure, embodiments of the present invention cancel out a rotation of array 64 by any angle θ by a rotation θ of the displayed image. The flowchart of FIG. 5 describes steps for cancelling rotation of array 64.

During a procedure, embodiments of the present invention also use images acquired by array 64 to apply texture mapping to a CT image of patient 22. The flowchart of FIG. 6, further below, describes steps for applying such texture mapping. The steps of the two flowcharts are independent of each other, and may be implemented concurrently.

Figure 5:
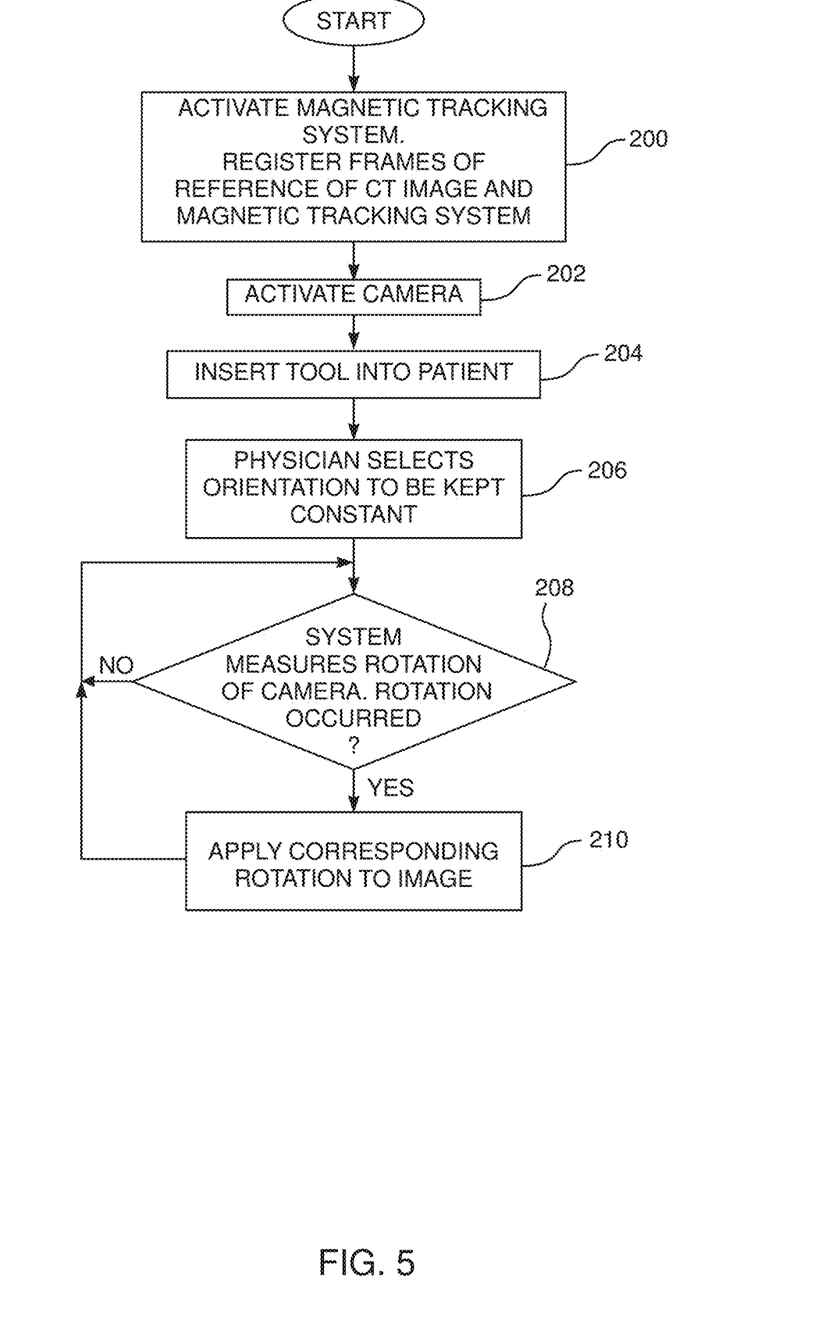
FIG. 5 is a flowchart of steps implemented to maintain an image generated by a camera in a desired orientation, according to an embodiment of the present invention.

FIG. 5 is a flowchart of steps implemented to maintain an image generated by camera 62 in a desired orientation, according to an embodiment of the present invention.

In an initial step 200 the frames of reference of magnetic tracking system 23 and a CT image of patient 22 are registered, as described above. In order to perform the registration, magnetic tracking system 23 is activated, and is used to track the positions and orientations of single axis coil 32 and dual axis coil 34, as is described above. The tracking is assumed to be updated in real time, so that by way of example in one embodiment system 23 is assumed to update its tracking data at a rate of 20 Hz, although the update rate may be slower or faster than this. Tool 21 may be used for the registration, with the signals from sensor 32 providing the 3D position of the distal tip of the tool. However, any other convenient method for registration may also be used.

In a camera activation step 202 physician 54 activates camera 62, so that optical video images generated by the camera are displayed to the physician on screen 56. Typically the images are circular, generally similar to circular section 138A (FIG. 4A). The images are updated in realtime, and by way of example in the description herein it is assumed that the images are generated and updated at the rate of 20 frames per second (fps), i.e., at the same rate as the tracking update. However, other embodiments of the invention may operate at slower or faster rates of frame generation. In cases where the tracking update is faster than the image update, the locations from the tracking update may be averaged to correspond to the image update.

In an insertion step 204 physician 54 inserts tool 21 into a nostril of patient 22. Once inserted, processor 40 displays video images of internal elements of patient 22 generated by camera 62 for viewing by the physician. The video images are displayed on screen 56.

In a select orientation step 206, the physician selects an orientation of the displayed image that is to be kept constant. Typically, the physician may make this selection by noticing that the displayed image has rotated so that it is in an unwanted orientation, then rotating tool 21 so that the image reverts to a desired orientation.

The physician makes the selection using controls 58, or another control, for example, a button that may be incorporated into a handle of tool 21. Activating the control transmits a command to processor 40 to begin measuring the rotation of camera 62 about its axis $y_a$, i.e., the axis orthogonal to array 64. It will be understood that, absent the following steps of the flowchart, rotation about axis $y_a$ would cause a displayed image rotation, such as those exemplified by image 130B and image 130C (FIGS. 4B and 4C).

In a rotation measurement comparison step 208, processor 40 measures consecutive changes of rotation of camera 62 about axis $y_a$, in at least one of two methods.

In a first method, processor 40 uses consecutive tracking signals from sensors 32 and 34 to decide if there has been a rotation about axis $y_a$ between the consecutive signals. As explained above, the signals from sensor 32 do not provide this information (because the axis of symmetry of sensor 32 is axis $y_a$); however it will be appreciated that the signals from sensor 34 do provide this information, since their axes of symmetry are orthogonal to axis $y_a$ when tubular section 84 is in its straight configuration 86. It will also be understood that the signals from sensor 34, if necessary taken with the signals from sensor 32, provide the required information even if tubular section 84 is bent from straight configuration 86 to curved configuration 88, when axis $y_a$ is not parallel to axis y.

In a second method, processor 40 compares consecutive images acquired by array 64, to determine if there has been an effective rotation between the images, about the center of the array in a plane of the array, i.e., orthogonal to the $y_a$ axis. To determine if there has been rotation processor 40 uses any convenient image processing method known in the art, such as that found at www.mathworks.com/help/images/find-image-rotation-and-scale-using-automated-feature-matching.html.

It will be understood that the comparison performed by the processor filters out other possible changes between the consecutive images, such as changes due to translation. Translation between consecutive images may be caused by physician 54 moving tool 21 from side to side with respect to an object being imaged.

If step 208 returns positive, i.e., the processor determines that rotation between consecutive images or consecutive tracking measurements has occurred, then in a cancellation step 210 the processor measures the rotation that has occurred, and applies a corresponding rotation to the image displayed on screen 56. The displayed image cancels out any rotation of camera 62.

In some embodiments both the first and the second rotation measurement method are used, in which case the measured rotation in step 210 may comprise an average of the rotations of both systems.

If step 208 returns negative, i.e., the processor determines that there is no rotation between consecutive images or consecutive tracking measurements, control returns to the beginning of step 208.

Processor 40 implements comparison step 208 iteratively during the course of the procedure performed by the physician, so that after the physician has selected in step 206 the displayed image orientation to be kept constant, any rotation of camera 62 about axis $y_a$ is cancelled out.

Figure 6:
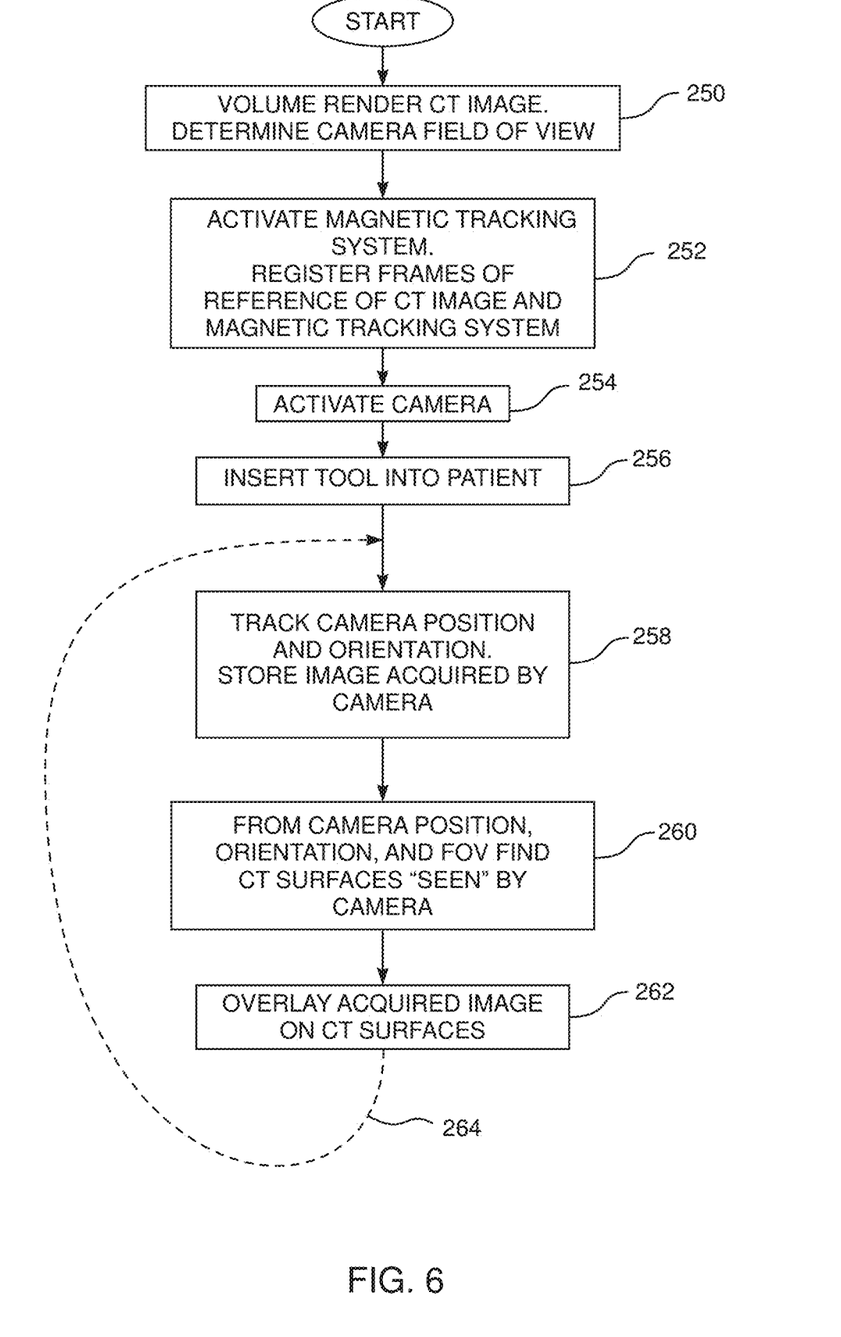
FIG. 6 is a flowchart of steps implemented to apply texture mapping to a CT image of a patient, according to an embodiment of the present invention.

FIG. 6 is a flowchart of steps implemented to apply texture mapping to a CT image of patient 22, and FIGS. 7, 8, 9, 10 are schematic figures describing aspects of the steps, according to an embodiment of the present invention.

In an initial preparatory step 250 processor 40 applies volume rendering to a CT image of patient 22. The processor may use any convenient method for volume rendering that is known in the art. In addition, the field of view (FOV) of camera 62 is also input to the processor.

Steps 252, 254, and 256 are respectively substantially as described above for steps 200, 202, and 204 of the flowchart of FIG. 5.

Figure 7:
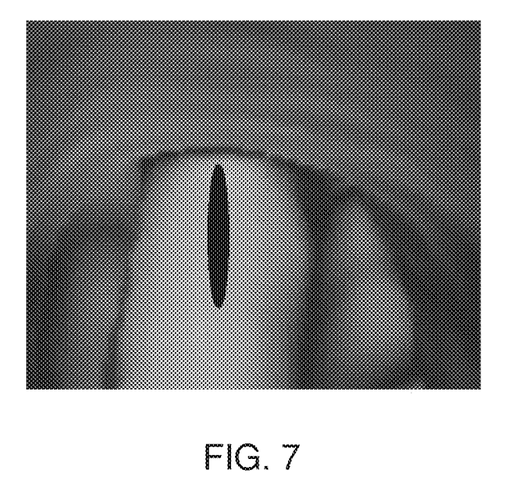
FIGS. 7, 8, 9, 10 are schematic figures describing aspects of the steps of the flowchart, according to an embodiment of the present invention.

In a track camera step 258, processor 40 acquires the position and orientation of camera 62, and stores the optical image acquired by the camera. The processor acquires the position and orientation of the camera using signals received from sensors 32 and 34. In the description herein, the orientation of the camera is assumed to include a direction towards which the camera is pointing, i.e., a camera view direction, when acquiring its image. FIG. 7 is a schematic illustration of an image acquired by the camera.

Step 258 is typically implemented by physician 54 providing a command to processor 40 to store the optical image acquired by camera 62. As is explained below, the acquired image is applied for texture imaging of the CT image. A typical scenario for implementing step 258 is the physician observing in the image acquired by the camera, a scene of interest, such as bleeding of an organ, on screen 56.

The following steps 260, 262, may be performed in real time, after completion of step 258. Alternatively or additionally, the following steps may be implemented at some time after step 258 has completed, for example by physician 54 reviewing the results of a completed procedure performed on patient 22.

In a surface determination step 260, processor 40 applies the position, orientation, and field of view (FOV) of the camera to the CT image to identify a section of a volume rendered surface of the CT image that is "seen" by the camera. The position and orientation of the camera are as found in step 258. The processor determines the FOV of the camera in step 250.

Figure 8:
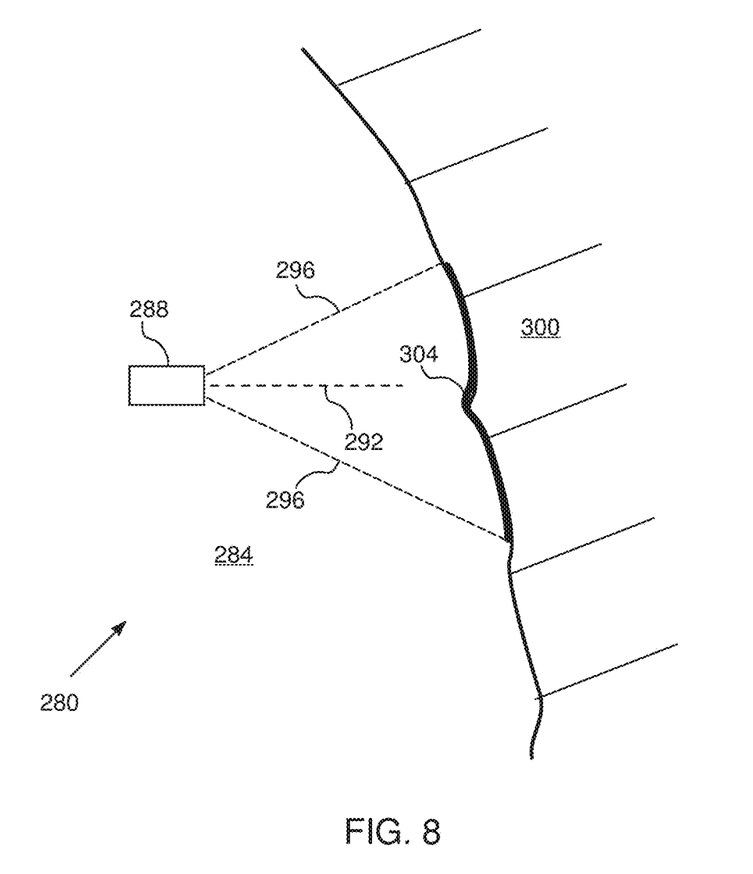

FIG. 8 is a schematic cross-sectional illustration of a section 280 of the CT image of patient 22, explaining the surface determination of step 260. On insertion of tool 21, the distal end of the tool, including camera 62, is typically in air, i.e., is in a transparent region 284 of CT image section 280, such as a cavity, having a Hounsfield Unit (HU) equal to zero. Since the frames of reference of the CT image and the magnetic tracking system, and thus of the camera, are registered, processor 40 applies the position and view direction of the camera to the CT image, so that in section 280 a rectangle 288 represents the camera, and a broken line 292 represents the camera view direction.

The FOV of the camera is illustrated by broken lines 296, and the processor extends the FOV lines until they connect to a section 300 of the CT image having non-zero HU values. Such a section typically comprises images of opaque elements such as bone or fat. Because the camera is in transparent region 284, a surface region 304, defined by the surface formed by FOV lines 296 meeting section 300, is the section of the CT image "seen" by the camera, and corresponds to the image of FIG. 7.

Figure 9:
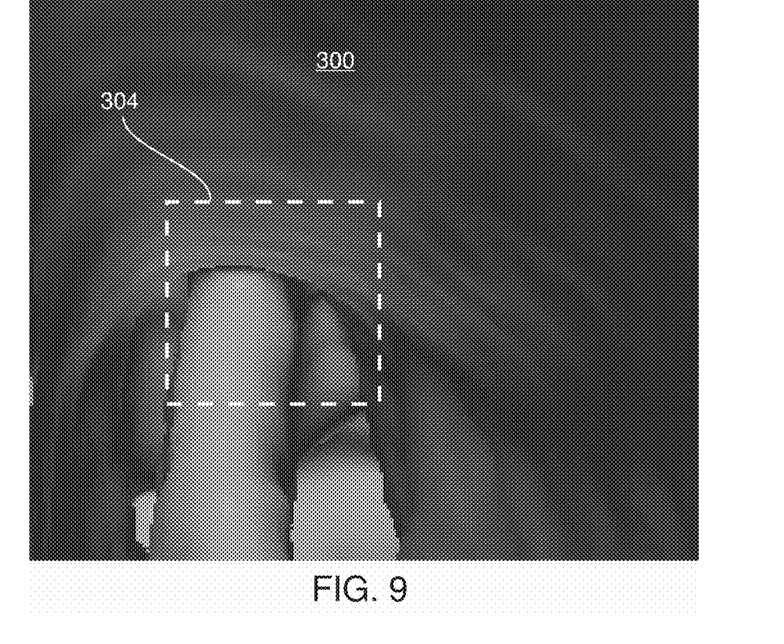

FIG. 9 illustrates CT image section 300, i.e., a section of the CT image having non-zero HU values, and surface region 304, formed by lines 296 meeting section 300.

Figure 10:
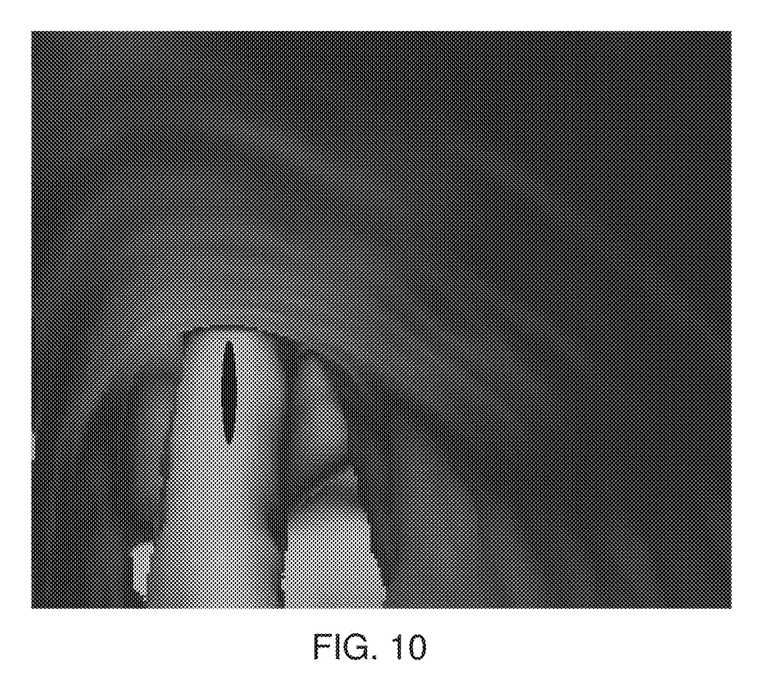

In an image overlay step 262, the processor overlays on CT surface section 304, the corresponding image acquired and stored in step 256, to produce a texture mapped image. FIG. 10 illustrates a texture mapped image, comprising the overlay of the image of FIG. 7 onto CT image section 300.

The description above of steps 258, 260, and 262 assumes a non-iterative process. However, in some embodiments steps 258, 260, and 262 may repeat, as indicated by broken arrow 264. A given repetition may be at the instigation of the physician, for example, on observation in the image acquired by the camera of another scene of interest. Alternatively or additionally, during at least part of the time during a procedure the physician may implement the repetition to be real-time repetition. In real-time repetition the texture mapping of the CT image may be updated on screen 56 continuously.

It will be appreciated from the description above that embodiments of the present invention comprise a single piece of apparatus that is configured to perform two different algorithms described by the flowchart of FIG. 5 and the flowchart of FIG. 6. The two algorithms are independent, and may be performed simultaneously or non-simultaneously by the single piece of apparatus.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. An apparatus, comprising:
   (a) a probe, configured to be inserted into an aperture of a human patient, the probe comprising:
      (i) an insertion tube comprising a distal section,
      (ii) a tubular deflectable section connected to the distal section of the insertion tube via a non-articulatable section,
      (iii) a camera, attached to the tubular deflectable section and having a direction of view,
      (iv) a first magnetic field sensor coil, which has a first coil axis of symmetry and is directly attached to the tubular deflectable section with the first coil axis parallel to the direction of view of the camera, and
      (v) a second magnetic field sensor coil, which has a second coil axis of symmetry and is directly attached to the non-articulatable section such that the second coil axis is perpendicular to the direction of view of the camera while the tubular deflectable section is aligned with the insertion tube, the second magnetic field sensor coil is located proximally relative to the first magnetic field sensor coil;
   (b) a display, coupled to display images output by the camera; and
   (c) a processor, which is coupled to receive signals generated by the first and second sensor coils in response to a magnetic field traversing the coils, and is configured:
      (i) in response to the signals received at a first time, to identify an initial orientation of an initial image produced by the camera,
      (ii) in response to the signals received at a second time, subsequent to the first time, to identify a subsequent orientation of a subsequent image produced by the camera, and
      (iii) to rotate the subsequent image on the display so as to reorient the subsequent image to the initial orientation.

2. The apparatus according to claim 1, and comprising a third magnetic field sensor coil which has a third coil axis of symmetry and which is attached to the insertion tube with the third coil axis perpendicular to the direction of view of the camera and to the second coil axis of symmetry, and wherein the signals received by the processor also comprise signals generated by the third sensor coil in response to the magnetic field traversing the third coil.

3. The apparatus according to claim 1, and comprising a flexible printed circuit board (PCB) fixedly positioned within the deflectable tubular section and wherein the camera is fixedly attached to a distal termination of the flexible PCB.

4. The apparatus according to claim 3, wherein the flexible PCB extends into the insertion tube.

5. The apparatus according to claim 1, wherein the processor is configured to determine a signal-based camera rotation in response to the signals received at the first and second times, and wherein the processor is further configured to compare and analyze the initial and the subsequent images so as to determine an image-based camera rotation, and wherein rotating the subsequent image comprises applying an average of the signal-based camera rotation and the image-based camera rotation to reorient the subsequent image.

6. The apparatus according to claim 5, wherein analyzing the initial and subsequent images comprises filtering the images to remove translation of the camera.

7. The apparatus according to claim 1, and comprising a magnetic tracking system generating the magnetic field, and wherein the processor is configured:
   (i) to register a computerized tomography (CT) image of the patient with the magnetic tracking system,
   (ii) to determine the direction of view and a position of the camera in response to the signals received at the second time,
   (iii) to receive an optical image acquired by the camera while the camera is directed towards the direction of view,
   (iv) to analyze the CT image, using the direction of view and the position of the camera, to find an opaque surface in the CT image that is in a field of view of the camera, and
   (v) to overlay the optical image on the opaque surface to texture map the opaque surface in the CT image.

8. A method for applying texture mapping to a computerized tomography (CT) image of a human patient, comprising:

(a) registering the CT image with a magnetic tracking system configured to track a magnetic field sensor in the patient;
(b) inserting a camera coupled to the magnetic field sensor into an aperture of the patient;
(c) determining a direction of view and a position of the camera in response to signals received from the magnetic field sensor;
(d) receiving an optical image acquired by the camera while the camera is directed towards the direction of view;
(e) analyzing the CT image, using the direction of view of the camera, a predetermined field of view of the camera, and the position of the camera, to find an opaque surface in the CT image that corresponds to the optical image acquired by the camera; and
(f) overlaying the optical image on the opaque surface to texture map the opaque surface in the CT image utilizing the position of the camera, the direction of view of the camera, and the predetermined field of view of the camera.

9. The method according to claim 8, wherein receiving the optical image comprises positioning the camera and the field of view of the camera in a transparent region.

10. A method, comprising:
(a) connecting a tubular deflectable section of a probe distally to an insertion tube of the probe, the insertion tube having a non-deflectable section;
(b) attaching a camera to the tubular deflectable section, the camera having a direction of view;
(c) attaching a first magnetic field sensor coil, which has a first coil axis of symmetry, directly to the tubular deflectable section with the first coil axis parallel to the direction of view of the camera while the tubular deflectable section is aligned with the insertion tube;
(d) attaching a second magnetic field sensor coil, which has a second coil axis of symmetry, directly to the non-deflectable section of the insertion tube with the second coil axis perpendicular to the direction of view of the camera, the second magnetic field sensor coil being proximal relative to the first magnetic field sensor coil;
(e) inserting the probe into an aperture of a human patient;
(f) providing a display, coupled to display images output by the camera;
(g) receiving signals generated by the first and second sensor coils in response to a magnetic field traversing the coils;
(h) in response to the signals received at a first time, identifying an initial orientation of an initial image produced by the camera;
(i) in response to the signals received at a second time, subsequent to the first time, identifying a subsequent orientation of a subsequent image produced by the camera; and
(j) rotating the subsequent image on the display so as to reorient the subsequent image to the initial orientation.

11. The method according to claim 10, and comprising attaching a third magnetic field sensor coil which has a third coil axis of symmetry to the insertion tube with the third coil axis perpendicular to the direction of view of the camera and to the second coil axis of symmetry, and wherein receiving the signals also comprises receiving signals generated by the third sensor coil in response to the magnetic field traversing the third coil.

12. The method according to claim 10, and comprising fixedly positioning a flexible printed circuit board (PCB) within the deflectable tubular section and fixedly attaching the camera to a distal termination of the flexible PCB.

13. The method according to claim 12, and comprising extending the flexible PCB into the insertion tube.

14. The method according to claim 10, and comprising determining a signal-based camera rotation in response to the signals received at the first and second times, comparing and analyzing the initial and the subsequent images so as to determine an image-based camera rotation, and wherein rotating the subsequent image comprises applying an average of the signal-based camera rotation and the image-based camera rotation to reorient the subsequent image.

15. The method according to claim 14, wherein analyzing the initial and subsequent images comprises filtering the images to remove translation of the camera.

16. The method according to claim 10, and comprising;
(a) generating the magnetic field with a magnetic tracking system;
(b) registering a computerized tomography (CT) image of the patient with the magnetic tracking system;
(c) determining the direction of view and a position of the camera in response to the signals received at the second time;
(d) receiving an optical image acquired by the camera while the camera is directed towards the direction of view;
(e) analyzing the CT image, using the direction of view and the position of the camera, to find an opaque surface in the CT image that is in a field of view of the camera; and
(f) overlaying the optical image on the opaque surface to texture map the opaque surface in the CT image.

17. An apparatus, comprising:
(a) a magnetic tracking system generating a magnetic field within a human patient;
(b) a probe, configured to be inserted into an aperture of the human patient;
(c) a camera, attached to the probe and having a direction of view;
(d) a magnetic field sensor coupled to the camera and configured to generate signals in response the magnetic field traversing the sensor;
(e) a display, coupled to display images; and
(f) a processor, which is coupled to receive the signals, and is configured:
(i) to register a computerized tomography (CT) image of the patient with the magnetic tracking system,
(ii) to determine the direction of view and a position of the camera in response to the signals,
(iii) to receive an optical image acquired by the camera while the camera is directed towards the direction of view,
(iv) to analyze the CT image, using the direction of view of the camera, a predetermined field of view of the camera, and the position of the camera, to find an opaque surface in the CT image that corresponds to the optical image acquired by the camera,
(v) to overlay the optical image on the opaque surface to texture map the opaque surface in the CT image, and
(vi) to present the texture mapped CT image on the display utilizing the position of the camera, the direction of view of the camera, and the predetermined field of view of the camera.

18. The apparatus according to claim 17, wherein receiving the optical image comprises positioning the camera and the field of view of the camera in a transparent region.

\* \* \* \* \*